(12) United States Patent
Ingram

(10) Patent No.: US 12,672,984 B2
(45) Date of Patent: Jul. 7, 2026

(54) NEGATIVE-PRESSURE THERAPY DRESSING WITH EXPANDABLE DEPTH

(71) Applicant: KCI Manufacturing Unlimited Company, Westmeath (IE)

(72) Inventor: Shannon C. Ingram, Bulverde, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 172 days.

(21) Appl. No.: 18/036,013

(22) PCT Filed: Oct. 20, 2021

(86) PCT No.: PCT/IB2021/059676
§ 371 (c)(1),
(2) Date: May 9, 2023

(87) PCT Pub. No.: WO2022/101719
PCT Pub. Date: May 19, 2022

(65) Prior Publication Data
US 2024/0016664 A1 Jan. 18, 2024

Related U.S. Application Data

(60) Provisional application No. 63/112,906, filed on Nov. 12, 2020.

(51) Int. Cl.
*A61F 13/05* (2024.01)
*A61F 13/00* (2024.01)
*A61M 1/00* (2006.01)

(52) U.S. Cl.
CPC ........ *A61F 13/05* (2024.01); *A61F 13/00995* (2013.01); *A61M 1/915* (2021.05)

(58) Field of Classification Search
CPC ... A61F 13/05; A61F 13/00995; A61M 1/915; A61M 1/916
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| (Continued) | | | |

FOREIGN PATENT DOCUMENTS

| | | |
|---|---|---|
| AU | 550575 B2 | 3/1986 |
| AU | 745271 B2 | 3/2002 |
| (Continued) | | |

OTHER PUBLICATIONS

International Search Report and Written Opinion corresponding to International Patent Application No. PCT/IB2021/059676, Mailed Feb. 14, 2022.

(Continued)

*Primary Examiner* — Ariana Zimbouski
*Assistant Examiner* — Matthew Wrubleski

(57) ABSTRACT

Disclosed embodiments relate to dressings for treating a tissue site with negative pressure. Some dressing embodiments may be configured to allow the depth of the dressing to be expandable. For example, dressing embodiments may comprise a segmented manifold having one or more vertical expansion joints between segments of the manifold. Some embodiments may comprise a first layer adjacent to a first surface of the manifold and a second layer adjacent to a second surface of the manifold. In some embodiments, the first layer may comprise one or more folds configured to extend between adjacent segments, and the second layer may also comprise one or more folds configured to extend between adjacent segments; and the folds in the first layer may match the folds in the second layer to jointly form the (Continued)

104

FIG. 5 vertical expansion joints. Additionally disclosed are other apparatus, dressings, systems, and methods.

26 Claims, 9 Drawing Sheets

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2014/0163491 A1 | 6/2014 | Schuessler et al. | |
| 2014/0163501 A1* | 6/2014 | Ehmsperger | ............ A61F 13/49 604/374 |
| 2015/0080788 A1 | 3/2015 | Blott et al. | |
| 2019/0117473 A1* | 4/2019 | Rosati | ................... A61F 13/515 |
| 2019/0175414 A1* | 6/2019 | Cavanaugh, II | ...... A61M 1/917 |
| 2020/0000985 A1* | 1/2020 | Seddon | ................... A61F 13/05 |

FOREIGN PATENT DOCUMENTS

| | | | | |
|---|---|---|---|---|
| AU | 755496 B2 | 12/2002 | | |
| CA | 2005436 A1 | 6/1990 | | |
| CA | 1294119 C | * 1/1992 | ........... A61F 13/474 |
| DE | 26 40 413 A1 | 3/1978 | | |
| DE | 43 06 478 A1 | 9/1994 | | |
| DE | 29 504 378 U1 | 9/1995 | | |
| EP | 0100148 A1 | 2/1984 | | |
| EP | 0117632 A2 | 9/1984 | | |
| EP | 0161865 A2 | 11/1985 | | |
| EP | 0358302 A2 | 3/1990 | | |
| EP | 1018967 A1 | 7/2000 | | |
| GB | 692578 A | 6/1953 | | |
| GB | 2195255 A | 4/1988 | | |
| GB | 2 197 789 A | 6/1988 | | |
| GB | 2 220 357 A | 1/1990 | | |
| GB | 2 235 877 A | 3/1991 | | |
| GB | 2 329 127 A | 3/1999 | | |

(56) References Cited

FOREIGN PATENT DOCUMENTS

| | | | |
|---|---|---|---|
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 2020046443 | A1 | 3/2020 |
| WO | 2020056182 | A1 | 3/2020 |
| WO | 2020081259 | A1 | 4/2020 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björm et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi Živadinovi?, V. ?uki? uki ?uki?, Ž. Maksimovi Maksimovi?, ?. Radak. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. @ Therapy Clinical Guidelines: A Reference Source for
Clinicians; Jul. 2007.

* cited by examiner

104

210

210

205

205

205

3

3

104

104

NEGATIVE-PRESSURE THERAPY DRESSING WITH EXPANDABLE DEPTH

CROSS-REFERENCE TO RELATED APPLICATIONS

This application claims the benefit of priority to U.S. Provisional Application No. 63/112,906, filed on Nov. 12, 2020, which is incorporated herein by reference in its entirety.

TECHNICAL FIELD

The invention set forth in the appended claims relates generally to tissue treatment systems and more particularly, but without limitation, to systems, dressings, and fillers for negative-pressure tissue treatment, and methods of using systems, dressings, and fillers for negative-pressure tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

Disclosed embodiments relate to dressings for treating a tissue site with negative pressure. Some dressing embodiments may be configured to allow the depth of the dressing to be expandable. For example, dressing embodiments may comprise a segmented manifold having one or more vertical expansion joints between segments of the manifold. The vertical expansion joints may be configured to allow for vertical movement of the segments, for example with adjacent manifold segments being configured to slide with respect to each other to adjust the depth of the dressing to fit a specific tissue site. In some embodiments, each vertical expansion joint may utilize a bellows concept to allow for vertical expansion. In some embodiments, the segments of the manifold may be formed by one or more dividing lines, and the vertical expansion joints may be configured to match the dividing lines. Some embodiments may comprise a first layer adjacent to a first surface of the manifold and a second layer adjacent to a second surface of the manifold. In some embodiments, the first layer may comprise one or more folds configured to extend between adjacent segments, and the second layer may also comprise one or more folds configured to extend between adjacent segments; and the folds in the first layer may match the folds in the second layer to jointly form the vertical expansion joints. In some embodiments, at least the first layer may comprise a plurality of fluid passages.

In some example embodiments, a dressing, for treating a tissue site with negative pressure, may comprise: a manifold comprising a first surface and a second surface opposite the first surface, wherein the manifold is segmented (e.g. further comprises a plurality of segments); a first layer adjacent to the first surface and a second layer adjacent to the second surface, the first layer and the second layer each comprising a polymer film; a plurality of fluid passages in the polymer film adjacent to at least the first surface; and one or more vertical expansion joints, wherein adjacent segments have one of the vertical expansion joints located therebetween and the vertical expansion joints are configured to allow vertical movement of the segments. In some embodiments, each segment of the manifold may be coupled to the first layer at the first surface and/or to the second layer at the second surface. In some embodiments, each of the vertical expansion joints may comprise a portion of the first layer between adjacent segments which is not coupled to the adjacent segments and a portion of the second layer between the adjacent segments which is not coupled to the adjacent segments. In some embodiments, for each of the vertical expansion joints in a first, non-extended configuration, the portion of the first layer between adjacent segments may extend along a sidewall of a first of the adjacent segments; the portion of the first layer between adjacent segments may extend along a sidewall of a second of the adjacent segments; the portion of the second layer between adjacent segments may extend along the sidewall of the first of the adjacent segments; and the portion of the second layer between adjacent segments may extend along the sidewall of the second of the adjacent segments. In some embodiments, for each of the vertical expansion joints, the portion of the first layer between adjacent segments and the portion of the second layer between adjacent segments may not be coupled to each other. In some embodiments, each of the vertical expansion joints may comprise a fluid bridge between adjacent segments, wherein the fluid bridge may be defined between the first layer and the second layer, may span a dividing line gap between the adjacent segments, and may be configured to allow fluid communication between the adjacent segments. In some embodiments, the segments may be formed by one or more dividing lines through the manifold. For example, the one or more dividing lines may form concentric shapes (e.g. radial), may form a spiral, or may form a grid.

In some example embodiments, a dressing may comprise: a segmented manifold; and one or more vertical expansion joints between segments of the manifold. Some embodiments may further comprise a first layer adjacent to a first surface of the manifold and a second layer adjacent to a second surface of the manifold. In some embodiments, the first layer may comprise one or more folds configured to extend between adjacent segments, and the second layer may comprise one or more folds configured to extend between adjacent segments, wherein the one or more folds in the first layer may match the one or more folds in the second layer to jointly form the one or more vertical expansion joints.

In some example embodiments, a system for providing negative-pressure therapy to a tissue site may comprise a negative-pressure source in fluid communication with one of the dressing embodiments described herein (e.g. having a segmented manifold and one or more vertical expansion joints between segments of the manifold). Some embodiments may further comprise a dressing interface, wherein the negative-pressure source is in fluid communication with the segmented manifold through the dressing interface.

In some example embodiments, a method of manufacturing a dressing, may comprise: providing a segmented manifold having a first surface and a second surface opposite the first surface; providing a first layer and a second layer; stacking the segmented manifold between the first layer and the second layer, with the first layer adjacent to the first surface and the second layer adjacent to the second surface; and attaching the first surface to the first layer and/or the second surface to the second layer; wherein portions of the first layer between adjacent segments are not bonded to the adjacent segments, and portions of the second layer between adjacent segments are not bonded to the adjacent segments. Some embodiments may further comprise forming one or more vertical expansion joints between adjacent segments. In some embodiments, forming vertical expansion joints may comprise forming the first layer and the second layer each with matching folds configured to extend between adjacent segments. Some embodiments may further comprise perforating at least the first layer to form a plurality of fluid passages in at least the first layer. Some embodiments may further comprise sealing a perimeter of the dressing. In some embodiments, the segmented manifold may comprise dividing lines between segments, and the method may further comprise forming the first layer and the second layer with profiles (e.g. folds) matching the dividing lines. In some embodiments, stacking the segmented manifold between the first and second layers may comprise aligning the profiles with the dividing lines.

In some example embodiments, a method, of using a dressing having a plurality of manifold segments with vertical expansion joints therebetween, may comprise: placing the dressing into proximity with a tissue site; vertically displacing one or more manifold segments so that the manifold segments are substantially in contact with the tissue site; and applying negative pressure through the manifold segments to the tissue site. In some embodiments, vertically displacing one or more segments may comprise pressing downward on the one or more manifold segments to slide adjacent segments vertically at the vertical expansion joints.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

Figure 1:
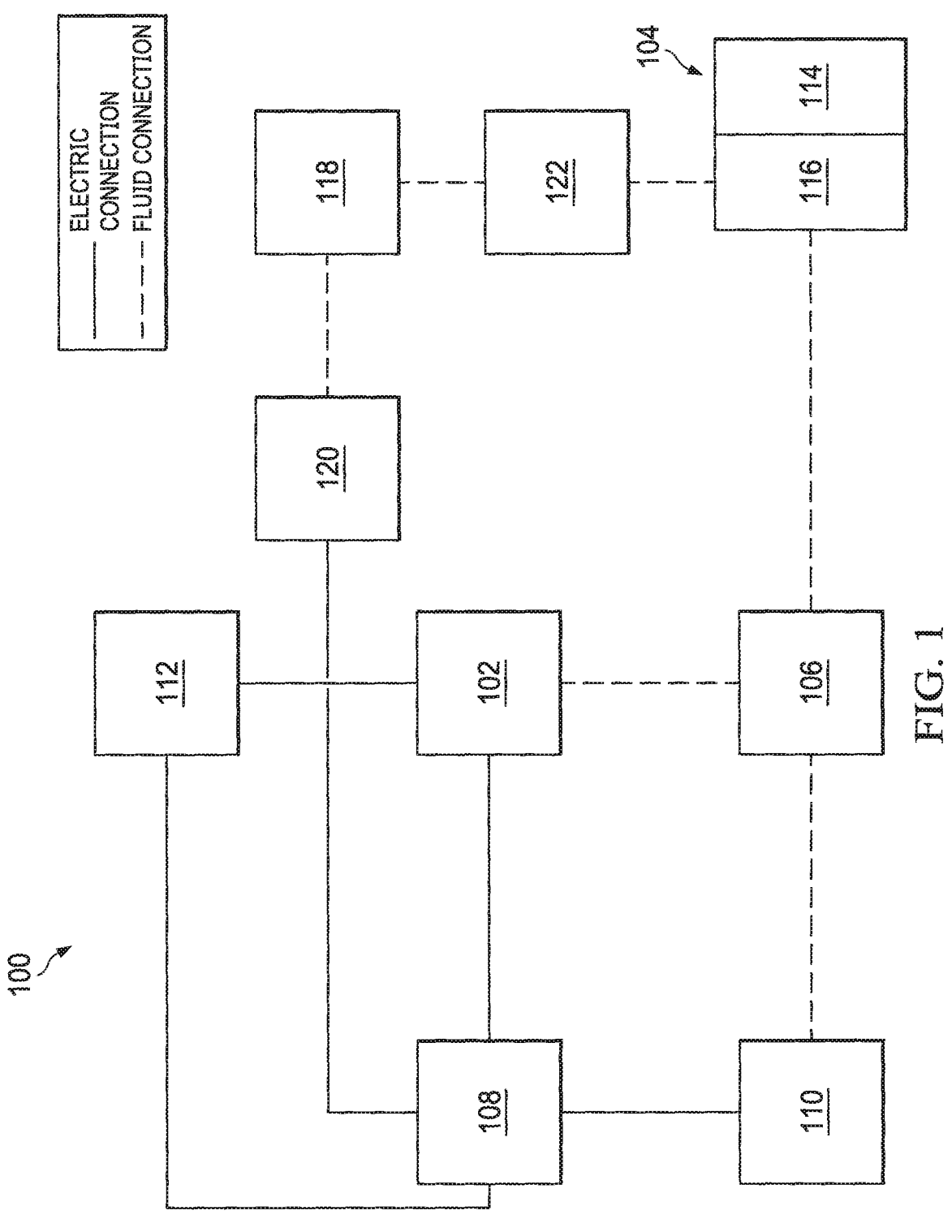
FIG. 1 is a block diagram of an example embodiment of a therapy system that can provide negative-pressure treatment in accordance with this specification.

FIG. 1 is a block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, the therapy system 100 may include one or more sensors, for example a pressure sensor 110, an electric sensor 112, or both, coupled to the controller 108. As illustrated in the example of FIG. 1, the dressing 104 may comprise or consist essentially of a tissue interface 114, a cover 116, or both in some embodiments.

The therapy system 100 may also include a source of instillation solution. For example, a solution source 118 may be fluidly coupled to the dressing 104, as illustrated in the example embodiment of FIG. 1. The solution source 118 may be fluidly coupled to a positive-pressure source such as the positive-pressure source 120, a negative-pressure source such as the negative-pressure source 102, or both in some embodiments. A regulator, such as an instillation regulator 122, may also be fluidly coupled to the solution source 118 and the dressing 104 to ensure proper dosage of instillation solution (e.g. saline) to a tissue site. For example, the instillation regulator 122 may comprise a piston that can be pneumatically actuated by the negative-pressure source 102 to draw instillation solution from the solution source during a negative-pressure interval and to instill the solution to a dressing during a venting interval. Additionally or alternatively, the controller 108 may be coupled to the negative-pressure source 102, the positive-pressure source 120, or both, to control dosage of instillation solution to a tissue site. In some embodiments, the instillation regulator 122 may also be fluidly coupled to the negative-pressure source 102 through the dressing 104, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the solution source 118, the controller 108, and other components into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 108, and may be fluidly coupled to one or more distribution components to provide a fluid path to a tissue site. In some embodiments, components may also be coupled by virtue of physical proximity, being integral to a single structure, or being formed from the same piece of material. For example, the tissue interface 114 and the cover 116 may be discrete layers disposed adjacent to each other, and may be joined together in some embodiments.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSA-T.R.A.C.™ Pad available from Kinetic Concepts, Inc. of San Antonio, Texas.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100.

Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, for example, the pressure sensor 110 may be a piezoresistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to partially or fully contact a tissue site. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. Any or all of the surfaces of the tissue interface 114 may have an uneven, coarse, or jagged profile.

In some embodiments, the tissue interface 114 may comprise or consist essentially of a manifold. A manifold in this context may comprise or consist essentially of a means for collecting or distributing fluid across the tissue interface 114 under pressure. For example, a manifold may be adapted to receive negative pressure from a source and distribute negative pressure through multiple apertures across the tissue interface 114, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 114 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 114 may also vary according to needs of a prescribed therapy. For example, the tensile strength of foam may be increased for instillation of topical treatment solutions. The 25% compression load deflection of the tissue interface 114 may be at least 0.35 pounds per square inch, and the 65% compression load deflection may be at least 0.43 pounds per square inch. In some embodiments, the tensile strength of the tissue interface 114 may be at least 10 pounds per square inch. The tissue interface 114 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 114 may comprise or consist essentially of reticulated polyurethane foam such as found in GRANUFOAM™ dressing or V.A.C. VERAFLO™ dressing, both available from Kinetic Concepts, Inc. of San Antonio, Texas.

The thickness of the tissue interface 114 may also vary according to needs of a prescribed therapy. For example, the thickness of the tissue interface may be decreased to reduce tension on peripheral tissue. The thickness of the tissue interface 114 can also affect the conformability of the tissue interface 114. In some embodiments, a thickness in a range of about 5 millimeters to 10 millimeters may be suitable.

The tissue interface 114 may be either hydrophobic or hydrophilic. In an example in which the tissue interface 114 may be hydrophilic, the tissue interface 114 may also wick fluid away from a tissue site, while continuing to distribute negative pressure to the tissue site. The wicking properties of the tissue interface 114 may draw fluid away from a tissue site by capillary flow or other wicking mechanisms. An example of a hydrophilic material that may be suitable is a polyvinyl alcohol, open-cell foam such as V.A.C. WHITE-FOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 114 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and caprolactones. The tissue interface 114 may further serve as a scaffold for new cell-growth, or a scaffold material may be used in conjunction with the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

Some embodiments of the tissue interface 114 may comprise layers, components, or features in addition to the manifold. For example, the tissue interface 114 may comprise a protective layer (e.g. a tissue-contact layer). In some embodiments, the protective layer may act as a comfort layer, configured to improve comfort at the tissue site. In some embodiments, the protective layer may act as a fluid control layer, configured to minimize maceration, backflow of exudate out of the dressing to the tissue site, and/or tissue in-growth from the tissue site into the dressing 104. The protective layer may be configured to allow fluid transport from the tissue site into the dressing 104 and/or to manifold during negative-pressure therapy. In some embodiments, the protective layer may be configured as the tissue-contact surface for the dressing, so that in use it may be located adjacent to and/or direct contact with the tissue site. In some embodiments, the protective layer may be located between the tissue-contact surface and the manifold and/or the absorbent layer. In some embodiments, the protective layer may be located between the tissue site (when the dressing is in use) and the manifold and/or absorbent layer.

In some embodiments, the protective layer may comprise a porous fabric, a porous film, or a polymeric film (e.g. which may be liquid impermeable) with a plurality of fluid passages (e.g. slits, slots, or fluid valves). In some embodiments, the protective layer may comprise or consist essentially of a woven, elastic material or a polyester knit textile substrate. As a non-limiting example, an InterDry™ textile material from Milliken Chemical of Spartanburg, South Carolina, may be used. The protective layer may also include anti-microbial substances, such as silver, in some embodiments.

In some embodiments, the protective layer may comprise or consist essentially of a liquid-impermeable, elastomeric material. For example, the protective layer may comprise or consist essentially of a polymer film. In some embodiments, for example, the protective layer may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. In some embodiments, the protective layer may be hydrophobic. In some embodiments, the protective layer may be hydrophilic. In some embodiments, the protective layer may be suitable for coupling, such as welding, to other layers, such as the manifold.

Some embodiments of the protective layer may have one or more fluid passages, which can be distributed uniformly or randomly across the protective layer. The fluid passages may be bi-directional and pressure-responsive. For example, each of the fluid passages generally may comprise or consist essentially of an elastic passage that is normally unstrained to substantially reduce liquid flow, and can expand or open in response to a pressure gradient. In some embodiments, the fluid passage may comprise or consist essentially of perforations in the protective layer. Perforations may be formed by removing material from the protective layer. For example, perforations may be formed by cutting through the protective layer, which may also deform the edges of the perforations in some embodiments. In the absence of a pressure gradient across the perforations, the passages may be sufficiently small to form a seal or fluid restriction, which can substantially reduce or prevent liquid flow. Additionally or alternatively, one or more of the fluid passages may be an elastomeric valve that is normally closed when unstrained to substantially prevent liquid flow, and can open in response to a pressure gradient. A fenestration may be a suitable valve for some applications. Fenestrations may also be formed by removing material from the protective layer, but the amount of material removed and the resulting dimensions of the fenestrations may be up to an order of magnitude less than perforations, and may not deform the edges.

For example, some embodiments of the fluid passages may comprise or consist essentially of one or more slits, slots or combinations of slits and slots in the protective layer. In some examples, the fluid passages may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may comprise or consist of, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 250 g/m^2 per twenty-four hours in some embodiments, measured using an upright cup technique according to ASTM E96/E96M Upright Cup Method at 38 degrees Celsius and 10% relative humidity. In some embodiments, an MVTR up to 5,000 grams per square meter per twenty-four hours may provide effective breathability and mechanical properties. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

The cover 116 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; an INSPIRE 2301 and INSPIRE 2327 material from Coveris Advanced Coatings of Wrexham, United Kingdom having, for example, an MVTR (inverted cup technique) of 14400 g/m2/24 hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); polyurethane (PU); EVA film; co-polyester; silicones; a silicone drape; a 3M Tegaderm® drape; a polyurethane (PU) drape such as one available from Avery Dennison Corporation of Glendale, California; polyether block polyamide copolymer (PEBAX), for example, from Arkema, France; INSPIRE 2327; or other appropriate material.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 118 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 114 may be placed within, over, on, or otherwise proximate to a tissue site. If the tissue site is a wound, for example, the tissue interface 114 may partially or completely fill the wound, or it may be placed over the wound. The cover 116 (e.g. a separate drape) may be placed over the tissue interface 114 and sealed to an attachment surface near a tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce pressure in the sealed therapeutic environment. A port may be applied to the cover, providing fluid communication between the external environment (e.g. the negative-pressure source 102) and the manifold of the dressing.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream"

implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Figure 2:
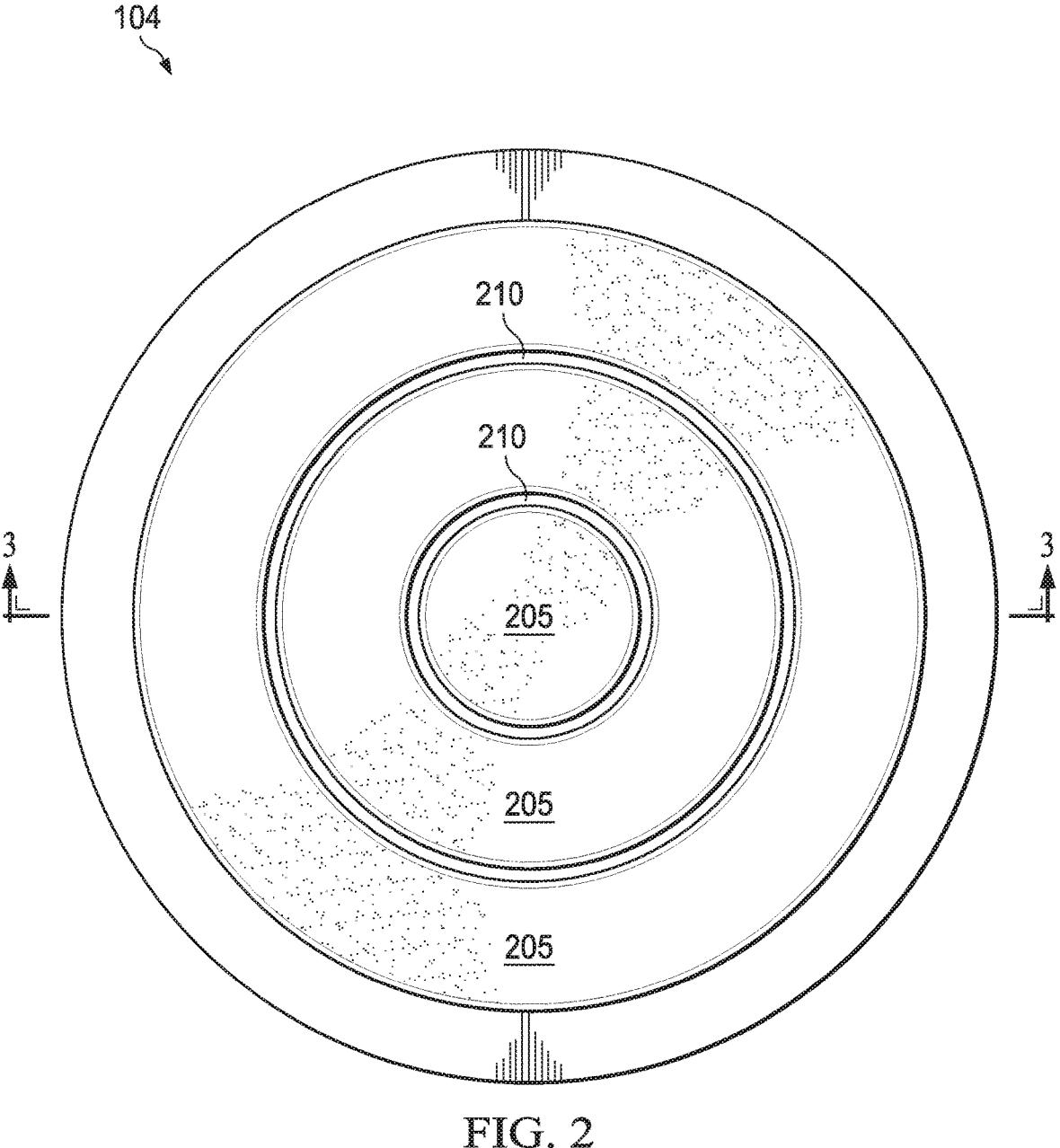
FIG. 2 is a top plan view of an example dressing that may be associated with an example embodiment of the therapy system of FIG. 1.
Figure 3:
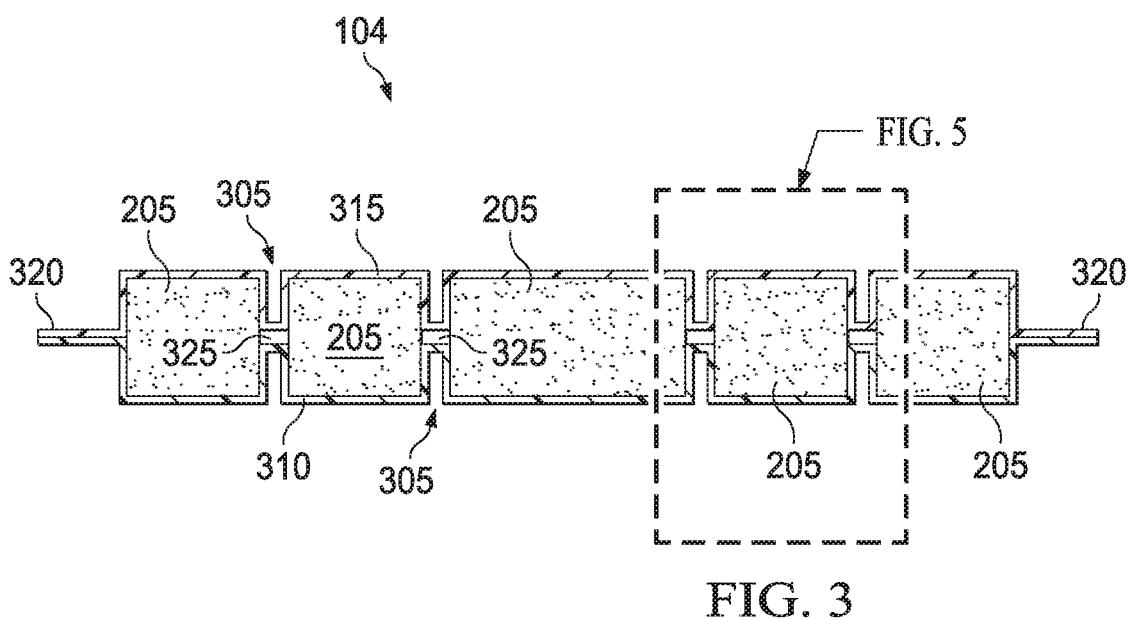
FIG. 3 is a cross-section view of the dressing of FIG. 2, illustrating additional details that may be associated with some embodiments.
Figure 4:
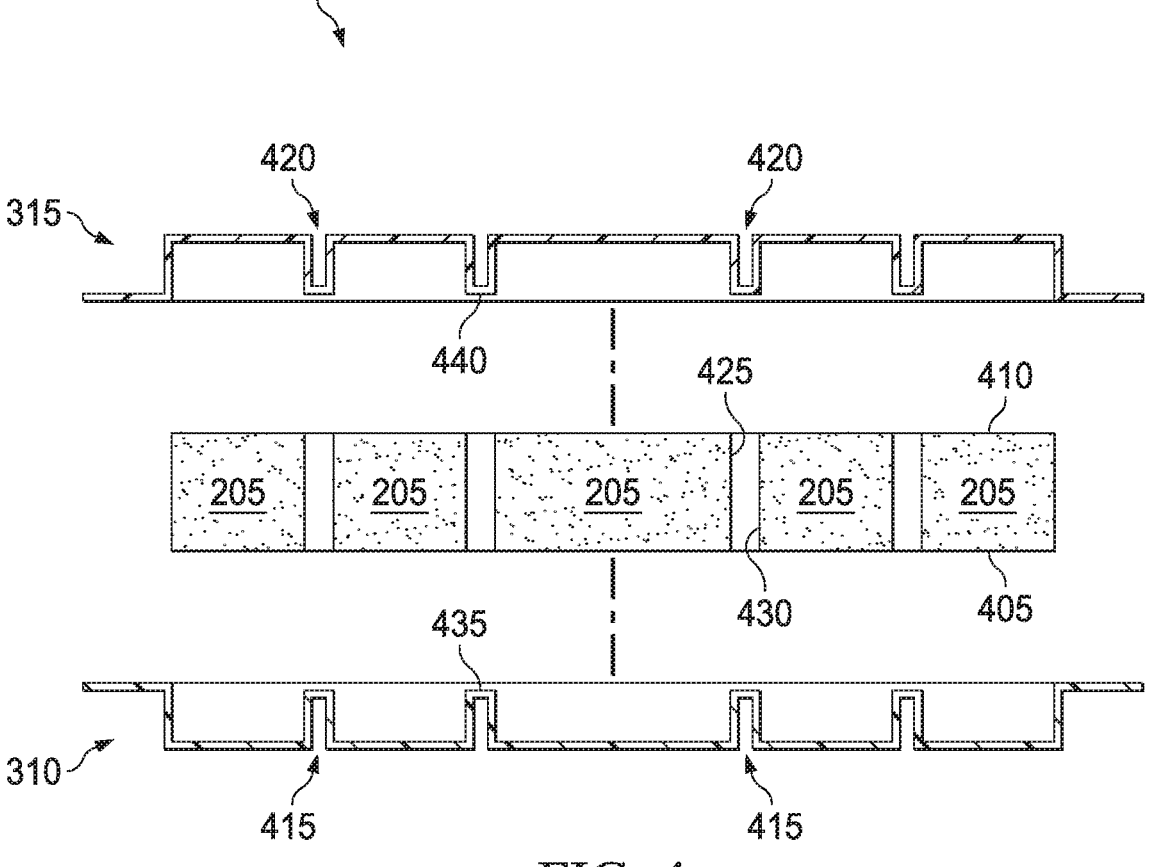
FIG. 4 is an exploded side elevation view of the dressing of FIG. 3, illustrating additional details that may be associated with some embodiments.

Referring to FIGS. 2-4, the dressing 104 may be configured in some embodiments to allow for adjustment of the depth of various portions or segments 205 of the dressing 104, for example to allow the dressing 104 to better fit the contours of a deep wound.

FIG. 2 is a top plan view of such an example dressing 104 that may be associated with an example embodiment of the therapy system 100 of FIG. 1. In some embodiments, the dressing 104 may comprise a segmented manifold. For example, the plurality of manifold segments 205 may be formed and/or defined by one or more dividing lines 210 through the manifold, and the manifold segments 205 may be configured with respect to one another to allow vertical displacement for depth adjustability. In some embodiments, the one or more dividing lines 210 may be cutting lines. For example, the manifold may be cut into segments 205, with each manifold segment 205 being separated from one or more other, adjacent manifold segments 205 by a dividing line 210 formed by the cutting process. In some embodiments, the one or more dividing lines 210 may form concentric shapes, and the adjacent segments 205 may be concentric. For example, in FIG. 2, the one or more dividing lines 210 may be radial (e.g. circular), and/or the adjacent segments 205 may be formed as rings (for example, centered around a common axis). In some embodiments, each of the manifold segments 205 may comprise open cell foam, such as polyurethane foam.

FIG. 3 is a cross-section view of the dressing 104 of FIG. 2, illustrating additional details that may be associated with some embodiments. As shown in FIG. 3, in some embodiments the dressing 104 may further comprise one or more vertical expansion joints 305, which may be configured to span the dividing lines 210 (shown in FIG. 2) between the manifold segments 205 and/or configured to allow vertical displacement of adjacent segments 205. In some embodiments, the vertical expansion joints 305 may be configured to match the dividing lines 210. For example, one of the vertical expansion joints 305 may be located between each pair of adjacent manifold segments 205 (e.g. spanning the gap between adjacent segments 205 formed by the dividing line 210 therebetween). In some embodiments, each of the vertical expansion joints 305 may be configured to allow vertical movement of the manifold segments 205 with respect to one another (e.g. with respect to adjacent segments 205), for example from a first (e.g. non-extended) configuration to a second (e.g. extended) configuration. In some embodiments, the vertical expansion joints 305 may be configured to allow adjacent segments 205 to slide vertically with respect to each other up to a pre-defined amount. In some embodiments, the vertical expansion joints 305 may be configured so that each manifold segment 205 may be displaced vertically up to a maximum of approximately its thickness (while in other embodiments, the amount of vertical displacement may be configured to be less than the full thickness, for example up to half the thickness of the manifold segment 205 or up to ¾ the thickness of the manifold segment 205). In some embodiments, the pre-defined amount of vertical sliding between adjacent segments 205 may be determined by the height/thickness of the manifold segments 205, the vertical location of the vertical expansion joint 305, the size of the vertical expansion joint 305 (e.g. the size of the bridge between adjacent segments 205), and/or the compressibility of the manifold segments 205. In some embodiments, the depth adjustability of the dressing 104 may be determined by the number of manifold segments 205, the location of the manifold segments 205 and/or dividing lines 210, the height/depth of the manifold segments 205, the vertical location of the vertical expansion joints 305, the size of the vertical expansion joints 305, and/or compressibility of the manifold segments 205.

In some embodiments, "vertical" may mean displacement direction with respect to depth, for example adjusting the depth of one manifold segment 205 with respect to other manifold segments 205 and/or the tissue site. In some embodiments, "vertical" may mean in a direction substantially orthogonal to the planar surfaces of the dressing 104 (e.g. a first surface and a second surface of the manifold and/or a first layer 310 and/or a second layer 315) and/or to the tissue site when the dressing 104 is in place on the tissue site. In some embodiments, the plurality of manifold segments 205 may be disposed (e.g. sandwiched) between the first layer 310 (which may be configured as a tissue-contact layer and/or configured to be oriented towards the tissue site) and the second layer 315 (e.g. opposite the first layer 310 and/or configured to face outward, away from the tissue site). In some embodiments, the first layer 310 and the second layer 315 may jointly contain the plurality of manifold segments 205 therebetween. For example, the first layer 310 and the second layer 315 may be coupled (e.g. bonded, such as by adhesive or weld) at a perimeter of the dressing 104, forming a sealed perimeter and enclosing the plurality of manifold segments 205 between the first layer 310 and the second layer 315. In some embodiments, coupling the first layer 310 and the second layer 315 about the perimeter may form a perimeter flange 320. While FIG. 3 illustrates the perimeter flange 320 located approximately at the center of the thickness of the manifold segments 205 (e.g. the center of an exterior sidewall of the dressing 104), in other embodiments the perimeter flange 320 may be located at the top, the bottom, or some other height therebetween.

In some embodiments, the first layer 310 and the second layer 315 may jointly encapsulate the manifold segments 205 and jointly form the one or more vertical expansion joints 305 between adjacent segments 205. For example, the first layer 310 and second layer 315 (e.g. bellows or fold portions of the layers) may jointly form the vertical expansion joints 305 between adjacent segments 205. In some embodiments, portions of the first layer 310 and portions of the second layer 315 may extend into the gap of the dividing line between adjacent segments 205, and may jointly form the vertical expansion joints 305. For example, each of the vertical expansion joints 305 may comprise a portion of the first layer 310 between adjacent segments 205 which is not bonded to the adjacent segments 205 (e.g. to their sidewalls), and a portion of the second layer 315 between the adjacent segments 205 which is not bonded to the adjacent segments 205 (e.g. to their sidewalls). In some embodiments, for each of the vertical expansion joints 305, the portion of the first layer 310 between adjacent segments 205 and the portion of the second layer 315 between adjacent segments 205 may not be directly coupled to each other or to the adjacent segments 205 (e.g. the sidewalls), such that the portion of the first layer 310 between adjacent segments, the portion of the second layer 315 between adjacent segments, and/or the adjacent segments 205 may be independently movable relative to one another. In some embodiments, for each vertical expansion joint 305, the portion of the first layer 310 between adjacent segments 205 and the portion of the second layer 315 between adjacent segments 205 may be configured to allow free sliding in the vertical direction. For example, the portion of the first layer 310 between adjacent segments 205 and the portion of the second layer 315 between adjacent segments 205 may be configured to provide some slack, for example with the first layer 310 and the second layer 315 each being sized larger than the corresponding exterior surface of the plurality of manifold segments 205. The amount of slack in the first and second layers 310, 315 between adjacent segments 205 may determine the amount of vertical movement such adjacent segments may have at the vertical expansion joint 305. In some embodiments, the first layer 310 and the second layer 315 may not be directly coupled (e.g. not bonded or adhered to each other), except at the perimeter.

Figure 5:
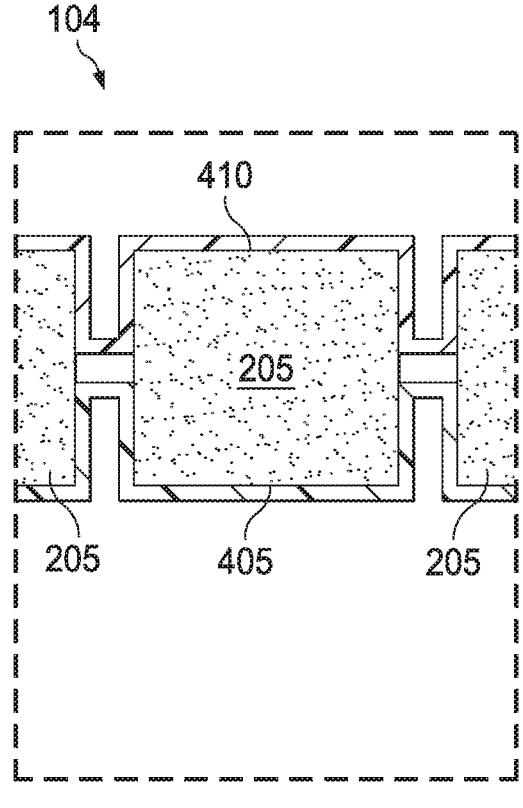
FIG. 5 is a partial schematic cross-section view of exemplary adjacent segments of the dressing of FIG. 3 in a first configuration, illustrating additional details that may be associated with some embodiments.
Figure 6:
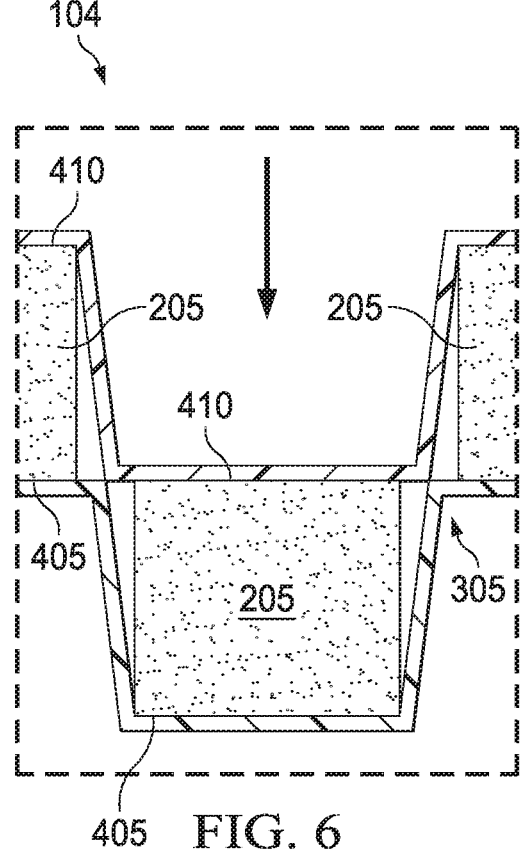
FIG. 6 is a partial schematic cross-section view of the exemplary adjacent segments of the dressing of FIG. 5 in a second configuration, illustrating additional details that may be associated with some embodiments.

In some embodiments, each of the vertical expansion joints 305 may comprise a fluid bridge 325 between adjacent segments 205. For example, the fluid bridge 325 may be defined between the first layer 310 and the second layer 315 (e.g. in a vertical space between the portions of the first layer 310 and the second layer 315 between adjacent manifold segments 205). The fluid bridge 325 for each vertical expansion joint 305 may span the gap of the dividing line 210 between the adjacent segments 205, and may be configured to allow fluid communication between the adjacent segments 205 (through the bridge, across the dividing line). In some embodiments, each vertical expansion joint 305 may be configured so that the fluid bridge 325 between adjacent segments 205 may move vertically as adjacent segments 205 move between the first configuration (e.g. as shown in FIG. 5) and the second configuration (e.g. as shown in FIG. 6). In some embodiments, the vertical space between the first layer 310 and the second layer 315 (e.g. formed by the uncoupled first and second layers 310, 315 between adjacent segments 205), may extend across the gap of the dividing line between adjacent segments 205, with the first layer 310 and the second layer 315 oriented substantially parallel to each other for at least a portion of the gap of the dividing line. In some embodiments, the vertical space may be sized to be about 3-6 mil, about 3 mil, or at least about 3 mil. In some embodiments, each fluid bridge 325 may be configured to maintain open space between the first layer 310 and the second layer 315 regardless of vertical expansion of manifold segments 205 (e.g. in the first configuration (flat or non-extended), the second configuration (fully extended), and in-between). In some embodiments, the fluid bridge 325 may be configured to maintain an open fluid pathway between adjacent segments 205 (e.g. not collapse) under negative pressure, such as during negative-pressure therapy. Although not shown here, some embodiments of the fluid bridge 325 may comprise an optional support feature (e.g. foam within the bridge, between the first layer 310 and the second layer 315 portions spanning the dividing line gap between adjacent segments 205), which may be configured to prevent collapse of the fluid bridge 325 under negative-pressure and/or to maintain open space between the first layer 310 and the second layer 315.

FIG. 4 is an exploded side elevation view of the dressing 104 of FIG. 3, illustrating additional details that may be associated with some embodiments. As shown in FIG. 4, the segmented manifold (e.g. the plurality of manifold segments 205) may comprise a first surface 405 and a second surface 410, opposite the first surface 405. In some embodiments, the first layer 310 may be disposed adjacent to the first surface 405 (e.g. tissue-facing or tissue-contact surface) and the second layer 315 may be adjacent to the second surface 410. In some embodiments, each segment 205 of the manifold may be coupled (e.g. bonded, such as by adhesive or welding) to the first layer 310 at the first surface 405 and/or to the second layer 315 at the second surface 410. In other embodiments, the manifold segments 205 may not be coupled (e.g. by adhesive or welding) to either the first layer 310 or the second layer 315 (e.g. the manifold segments 205 in some embodiments may be contained between the layers without being coupled to the layers). For example, first layer 310 and the second layer 315 may only be bonded to each other around the perimeter of the dressing 104 (e.g. forming the perimeter flange 320), with the first layer 310, the second layer 315, and the plurality of manifold segments 205 otherwise free to slide and/or reposition relative to one another. In some embodiments, each of the dividing lines 210 may extend completely between adjacent segments 205, for example completely through the manifold from the first surface 405 to the second surface 410, and may form separate segments 205 of the manifold (e.g. the separate manifold segments 205 may be separated by the dividing lines 210).

In some embodiments, each portion of the first layer 310 between adjacent segments 205 may form a first fold 415 in the first layer 310, and each portion of the second layer 315 between adjacent segments 205 may form a second fold 420 in the second layer 315. For example, in a first, non-extended configuration of the dressing 104, the first layer 310 may comprise one or more folds 415 configured to extend between adjacent segments 205 (e.g. at some depth between the adjacent segments 205), and the second layer 315 may comprise one or more folds 420 configured to extend between adjacent segments 205, wherein the one or more folds 415 in the first layer 310 may match, correspond to, be positioned across from, and/or be vertically aligned with the one or more folds 420 in the second layer 315 to jointly form the one or more vertical expansion joints 305. In some embodiments (for example, in the first configuration), the folds 415, 420 may provide sufficient slack (e.g. extra material of the first and second layers 310, 315 which is not stretched taut over the dividing lines) to allow vertical movement of the vertical expansion joints 305 from the first configuration to the second configuration. In some embodiments, the corresponding (e.g. matching) folds of the first layer 310 and second layer 315 may jointly form the fluid bridges 325 between adjacent segments 205.

In some embodiments, for each of the vertical expansion joints 305 in a first (e.g. non-extended) configuration, the portion of the first layer 310 between adjacent segments 205 may extend (e.g. upward) along a sidewall 425 of a first of the adjacent segments 205 (e.g. for less than half the thickness of the segment and/or the height of the sidewall); the portion of the first layer 310 between adjacent segments 205 may extend (e.g. downward) along a sidewall 430 of a second of the adjacent segments 205 (e.g. for less than half the thickness of the segments 205 and/or the height of the sidewall); the portion of the second layer 315 between adjacent segments 205 may extend (e.g. downward) along the sidewall 425 of the first of the adjacent segments 205 (e.g. for less than half the thickness of the segment and/or the height of the sidewall); and the portion of the second layer 315 between adjacent segments 205 may extend (e.g. upward) along the sidewall 430 of the second of the adjacent segments 205 (e.g. for less than half the thickness of the segment and/or of the sidewall). In some embodiments, portions of a layer extending along a sidewall may extend approximately parallel to the sidewall.

In some embodiments, a bridge portion 435 of the first layer 310 may connect the portion of the first layer 310 extending (e.g. upward) along the sidewall 425 of the first adjacent segment 205 to the portion of the first layer 310 extending (e.g. downward) along the sidewall 430 of the second adjacent segment 205; and a bridge portion 440 of the second layer 315 may connect the portion of the second layer 315 extending (e.g. downward) along the sidewall 425 of the first adjacent segment 205 to the portion of the second layer 315 extending (e.g. upward) along the sidewall 430 of the second adjacent segment 205. In some embodiments, bridge portion 435 of the first layer 310 and bridge portion 440 of the second layer 315 may jointly form the fluid bridges between adjacent segments 205 and may span the gap of the dividing lines 210 (as shown in FIG. 2).

In some embodiments, each of the vertical expansion joints 305 may comprise a bellows or may be configured to allow bellows expansion and/or to function as a bellows. For example, each of the bellows may comprise a top bellows portion and a bottom bellows portion. In some embodiments, the top bellows portion for each vertical expansion joint 305 may comprise and/or be formed by the portion of the second layer 315 between the adjacent segments 205 and/or spanning the dividing line, for example comprising the fold 420 in the second layer 315. In some embodiments, the bottom bellows portion for each vertical expansion joint 305 may comprise and/or be formed by the portion of the first layer 310 between the adjacent segments 205 and/or spanning the dividing line, for example comprising the fold 415 in the first layer 310.

In some embodiments, the manifold segments 205 may comprise open-cell foam. In some embodiments, each manifold segment 205 may have a thickness of approximately 5-10 mm. In some embodiments, the vertical expansion joints 305 may allow the dressing 104 to be used in wound cavities having a depth greater than the thickness of the manifold segments 205 (and in some instances, several times greater at portions), for example with the first layer 310 in proximity to the tissue site. In some embodiments, the first layer 310 and the second layer 315 may each comprise a polymer film, such as polyurethane film. In some embodiments, the first layer 310 and/or the second layer 315 may be configured to allow fluid flow therethrough. For example, the first layer 310 and/or the second layer 315 may not include a polymer film, but for example may be formed of a protective layer, such as a porous (e.g. woven) fabric. In some embodiments, the second layer 315 may be configured to allow expansion at the vertical expansion joints 305, even though the second layer 315 may not match the dividing line pattern. In some embodiments, the vertical expansion joints 305 may comprise elastic and/or stretchable portions (e.g. configured to provide significant stretch), which may be aligned on top and bottom and/or with the dividing lines 210. For example, the vertical expansion joints 305 may comprise a material configured to stretch and to take a set (e.g. to maintain the stretch), in some embodiments. In some embodiments, the dividing lines 210 may not pass entirely through the manifold; rather, partial cuts may define the manifold segments 205.

FIG. 5 is a partial schematic cross-section view of adjacent segments 205 of the dressing 104 of FIG. 3 in a first (e.g. non-extended) configuration, illustrating additional details that may be associated with some embodiments. In some embodiments, each adjacent pair of manifold segments 205 may comprise a first configuration in which the manifold segments 205 are non-extended (e.g. not vertically displaced). For example, in FIG. 5, the first configuration may have the adjacent segments 205 disposed lateral, flat, planar, and/or horizontally adjacent. For example, in FIG. 5 the first surface 405 of the adjacent segments 205 may be approximately aligned and the second surface 410 of the adjacent segments 205 may be approximately aligned. The vertical expansion joints 305 may be configured to allow reconfiguration of the adjacent segments 205 from the first configuration to a vertically displaced (e.g. vertically offset and/or extended) second configuration.

FIG. 6 is a partial schematic cross-section view of the adjacent segments 205 of the dressing 104 of FIG. 5 in the second (e.g. extended) configuration, illustrating additional details that may be associated with some embodiments. In FIG. 6, one of the manifold segments 205 of a pair of adjacent segments 205 may extend and/or be displaced vertically with respect to the adjacent one or more segments 205. For example, after a downward force has been applied to the manifold segment 205, the segment 205 may be extended downward up to its fullest extent, for example with the vertical expansion joint 305 (e.g. bellows) fully expanded. In some embodiments of the second configuration, the segments 205 may be vertically offset by all or some portion of the thickness of the segments 205. For example, as shown in FIG. 6, the first surface 405 of the adjacent segments 205 may be approximately parallel but not aligned, and the second surface 410 of the adjacent segments 205 may be approximately parallel but not aligned. In some embodiments, the second surface 410 of the displaced segment may be aligned with the first surface 405 of the adjacent segment. In some embodiments, when in the second configuration, the displaced segment 205 may be able to be return to the first configuration. For example, the vertical expansion joints 305 may be configured to allow the adjacent pairs to transition between the first and second configurations, and/or back again.

In FIG. 6, one of the manifold segments 205 may be adjacent to and between two other manifold segments 205, with a vertical expansion joint 305 located on both sides (e.g. between both pairs of adjacent segments 205). This may occur for any interior manifold segment, while exterior segments (e.g. along the perimeter) may not be located between two manifold segments 205 in some embodiments. In some embodiments, the polymer film of the first layer 310 and second layer 315 may be sufficiently flexible to allow repositioning between the first and second configurations. While the first configuration of the dressing 104 is shown in FIG. 5 as being approximately flat and/or planar, in other embodiments the first configuration may not be flat. For example, the dressing 104 may be pre-shaped with a non-flat first configuration (e.g. as a bowl), and the second configuration may allow adjacent segments 205 to be further displaced and/or extended vertically (e.g. to alter depth) from the initial position of the first configuration.

Figure 7:
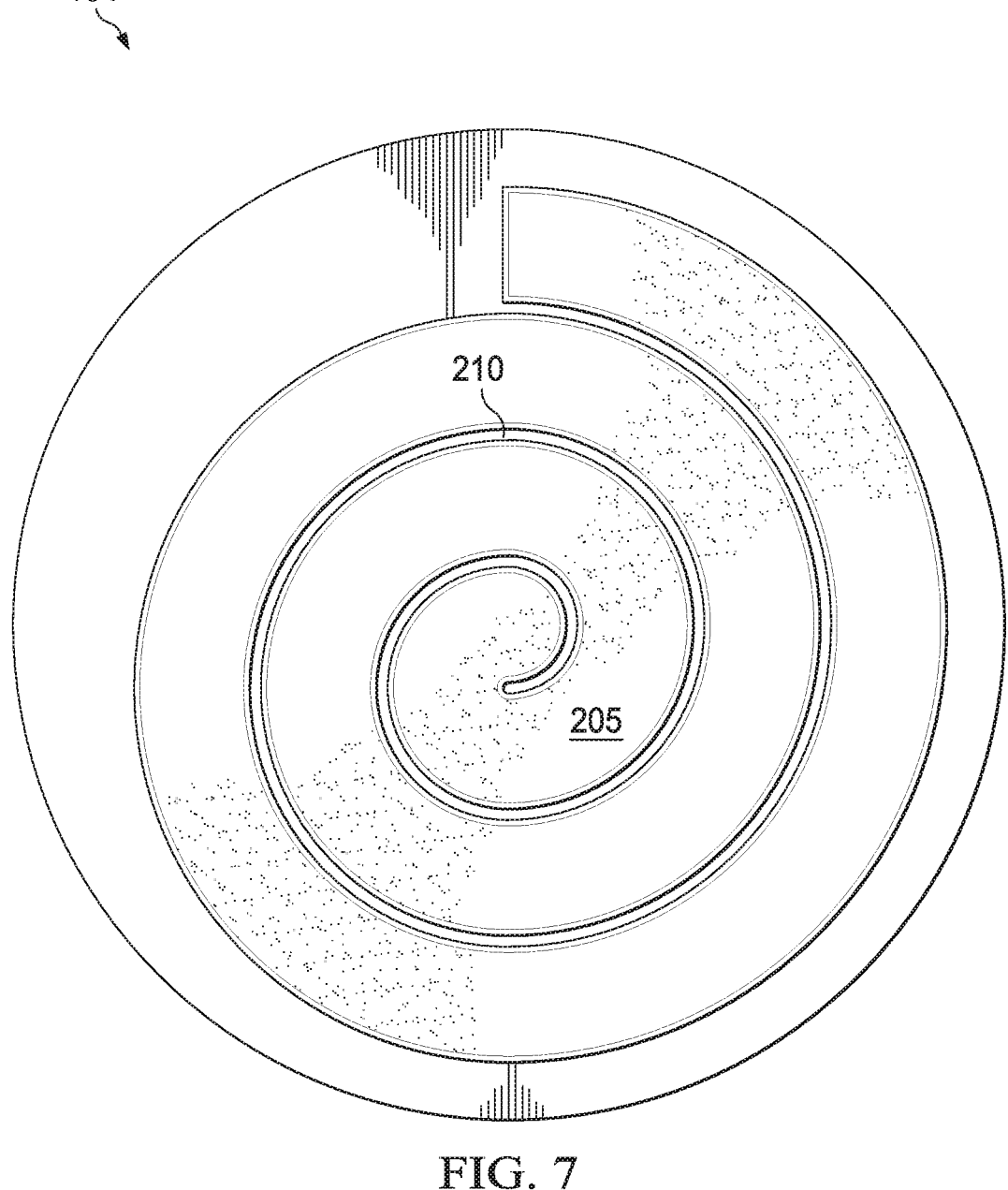
FIG. 7 is a plan view of another example dressing that may be associated with an example embodiment of the therapy system of FIG. 1.

FIG. 7 is a plan view of another example dressing 104 that may be associated with an example embodiment of the therapy system 100 of FIG. 1. FIG. 7 illustrates a dressing 104 in which the dividing line 210 forming the manifold segments 205 may be a spiral. Otherwise, the embodiment of FIG. 7 may be similar to that of FIG. 2. In FIG. 7, a single, elongate, spiral-shaped dividing line 210 may radially separate manifold segments 205, and the vertical expansion joint 305 spanning the dividing line 210 may allow for adjustment of the depth of the dressing 104 as discussed herein. For example, the dividing line 210 may form a spiral, and the manifold may form a spiral pattern with one, long continuous manifold element oriented in a spiral configuration and the spiral dividing line 210 segmenting the manifold radially to form radial manifold segments 205.

Figure 8:
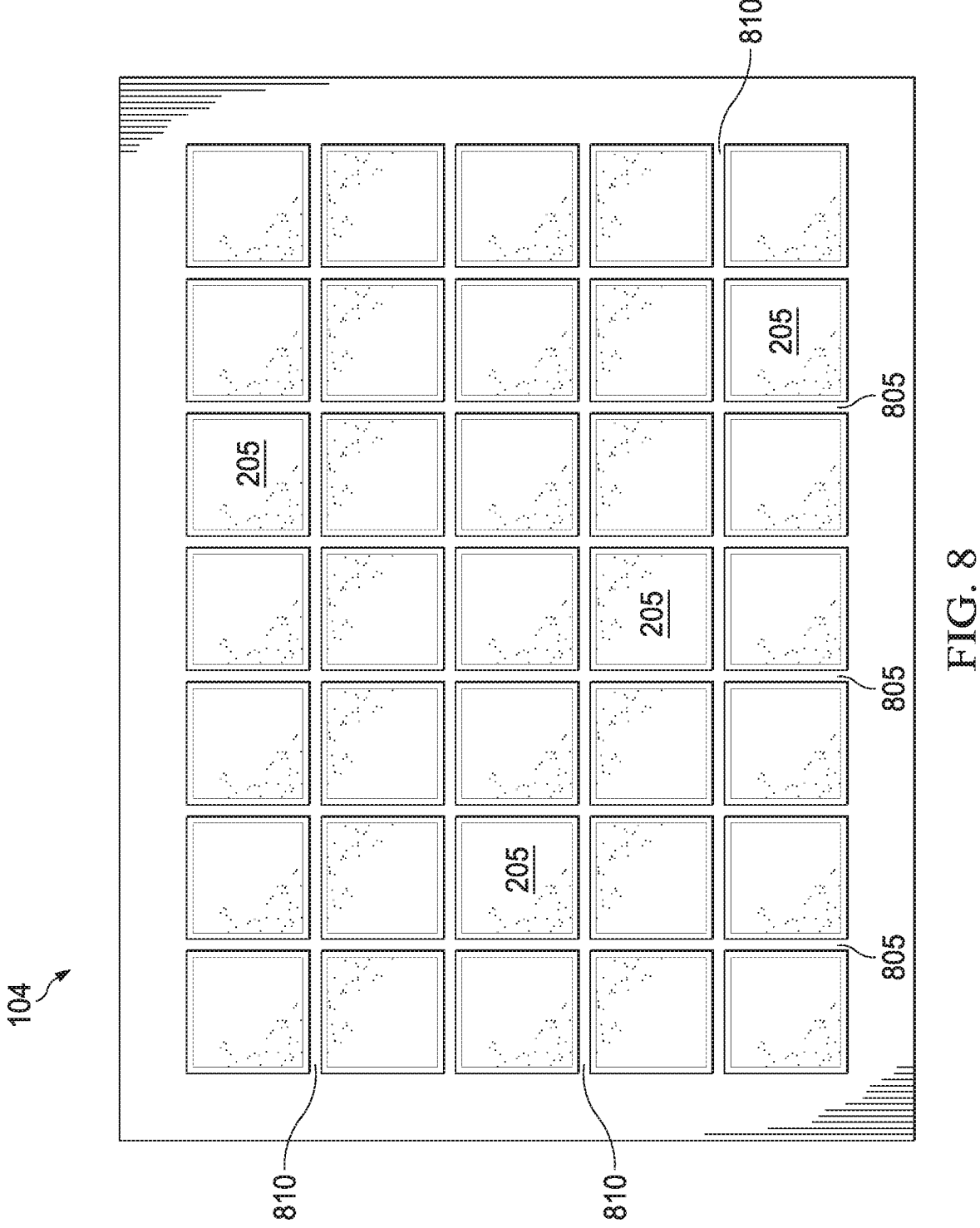
FIG. 8 is a plan view of yet another example dressing that may be associated with an example embodiment of the therapy system of FIG. 1.

FIG. 8 is a plan view of yet another example dressing 104 that may be associated with an example embodiment of the therapy system 100 of FIG. 1. FIG. 8 illustrates a dressing 104 in which the dividing lines 210 forming the manifold segments 205 may be a grid. For example, the dividing lines 210 may comprise one or more lines that are orthogonal to each other. In some embodiments, the dividing lines 210 may comprise a first plurality of lines 805, which may be approximately parallel, running in a first direction (e.g. across the second surface 410 of the manifold segments 205), and a second plurality of lines 810, which may be approximately parallel, running in a second direction. In some embodiments, the first direction may be perpendicular to the second direction. Other than the dividing line alignment, the embodiment of FIG. 8 may be similar to that of FIG. 2. In some embodiments, the one or more dividing lines 210 may form a grid between manifold segments 205 and/or the segments 205 may form a checkerboard pattern. In FIG. 8, the checkerboard pattern may comprise square-end (e.g. block) segments 205. In other embodiments, the segments 205 may form different patterns, so long as the dividing lines 210 segment the manifold and the vertical expansion joints 305 are configured to span the dividing lines 210 in such a way as to allow vertical displacement of adjacent segments 205 with respect to each other. For example, the segments 205 may each have a cylindrical shape in some embodiments, with wavy dividing lines 210 forming circle-end segments 205 (not shown here).

Figure 9:
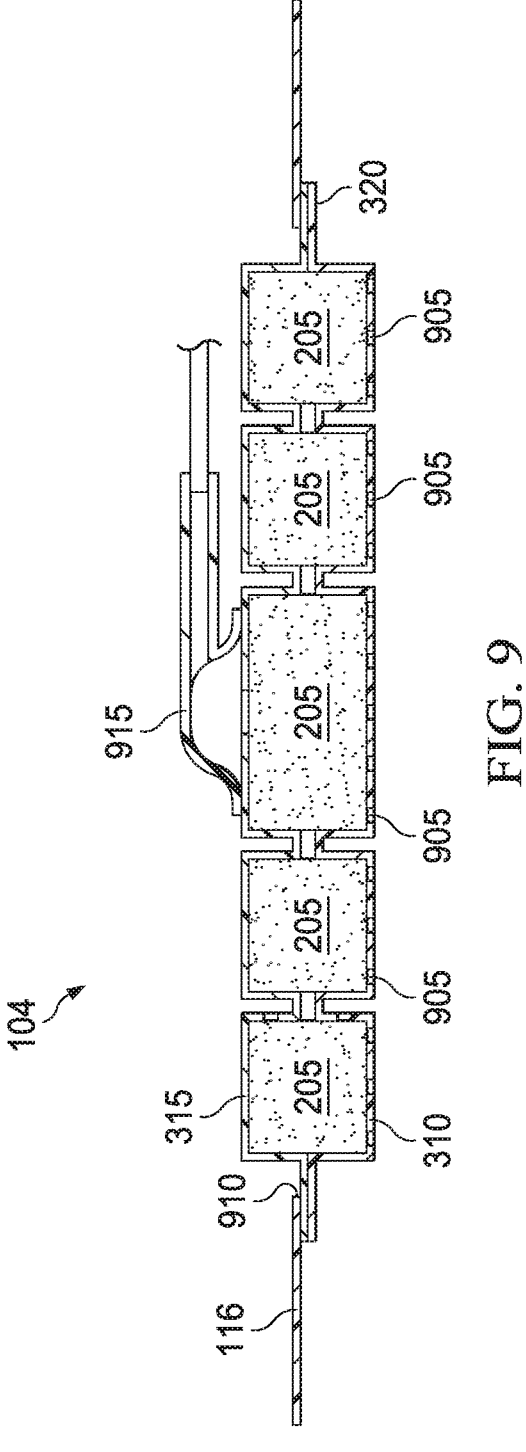
FIG. 9 is a schematic cross-section view of an example dressing, which may be similar to FIG. 3, ready for attachment to a tissue site for negative-pressure therapy.

FIG. 9 is a schematic cross-section view of an example dressing 104, which may be similar to FIG. 3, ready for attachment to a tissue site for negative-pressure therapy. In some embodiments, the first layer 310 may be configured to allow fluid communication between the manifold segments 205 and the tissue site during negative-pressure therapy. In some embodiments, the first layer 310 may be similar to a protective layer. For example, the first layer 310 may comprise a polymer film, such a polyurethane film, with a plurality of fluid passages 905 (e.g. similar to those described with respect to some protective layer embodiments). In some embodiments, the second layer 315 may be similar to and/or serve as the cover for the dressing 104, for example being fluid impermeable and/or configured to provide a seal adequate to maintain negative pressure during negative-pressure therapy at the tissue site. For example, the second layer 315 may comprise a polymer film, such as polyurethane film, without any fluid passages. In some embodiments, a dressing interface 915 may fluidly couple to the manifold segments 205 through the second layer 315 (e.g. fluidly couple to one of the manifold segments 205, and thereby be in fluid communication with the other manifold segments 205, for example through the fluid bridges 325 across the dividing lines 210). An adhesive drape or cover 116 may be attached around the perimeter of the dressing 104 (e.g. to adhere the dressing 104 in place on the tissue site and/or to seal the perimeter of dressing 104 to the tissue site), but in some embodiments may not span a central portion of the second layer 315. For example, the cover 116 may have an aperture 910 (e.g. configured to fit around the dressing 104 and to overlap the perimeter flange 320) so that it may only attach to the perimeter of the second surface 410. In some embodiments, the cover 116 may be configured to seal the perimeter of the dressing 104 to the tissue site.

Figure 10:
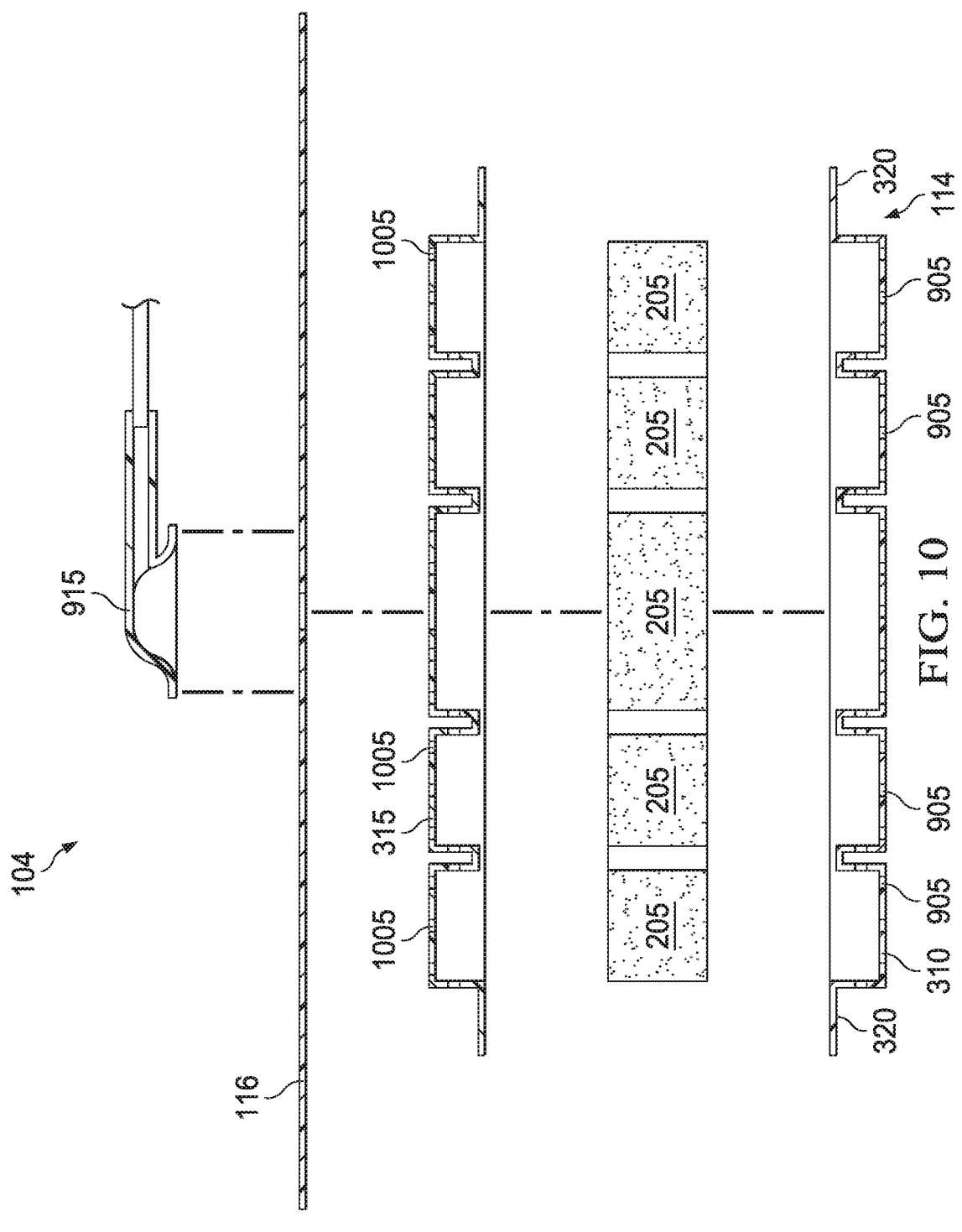
FIG. 10 is an exploded schematic cross-section view of another example dressing, which may be similar to FIG. 3, ready for attachment to a tissue site for negative-pressure therapy.

FIG. 10 is an exploded schematic cross-section view of another example dressing 104, which may be similar to FIG. 9 (but may also have a second plurality of fluid passages 1005 in the second layer 315), ready for attachment to a tissue site for negative-pressure therapy. In some embodiments, the segmented manifold and encapsulating first layer 310 and second layer 315 may form only the tissue interface 114 portion of the dressing 104. For example, a separate cover 116 may be needed to seal the tissue site, for example by being applied over the tissue interface 114 and/or spanning substantially the entire second surface 315. In some embodiments, both the first layer 310 and the second layer 315 may be fluid permeable and/or configured to allow fluid communication into and/or out of the manifold segments 205 during negative-pressure therapy. For example, both the first layer 310 and the second layer 315 may comprise polymer film, such as polyurethane film, having a plurality of fluid passages (e.g. with the first layer 310 having a first plurality of fluid passages 905, and the second layer 315 having a second plurality of fluid passages 1005). A separate cover 116, which may be a solid sheet or film, may be configured to be disposed over and/or to span the entire exposed tissue interface 114 (e.g. substantially the entire second layer 315 and/or all manifold segments 205), in some embodiments. In some embodiments, the attachment device for affixing the cover 116 may be located around the perimeter of the cover 116, and may not seal over the second plurality of fluid passages 1005. Some embodiments may have a dressing interface 915 configured to provide negative pressure to the manifold segments 205, for example through the cover 116.

In either FIG. 9 or FIG. 10, a negative-pressure source (not shown here) may be fluidly coupled to the dressing, for example via the dressing interface 915. The negative-pressure source may be configured for negative-pressure therapy. For example, the negative-pressure source may be configured to provide negative pressure to a tissue site through the dressing embodiments, even when the dressing 104 is in its second, extended configuration.

Figure 11:
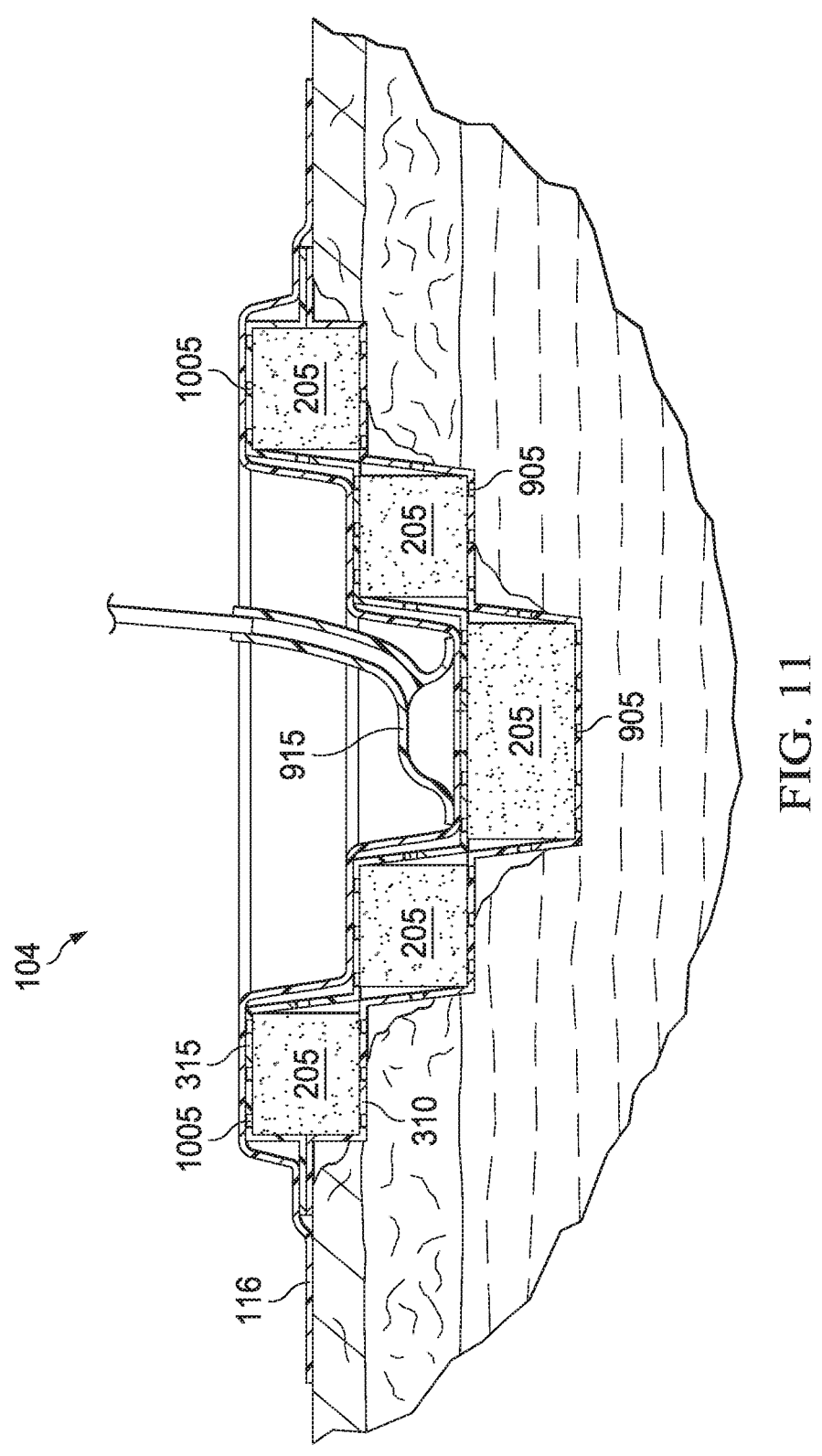
FIG. 11 is a schematic cross-section of an example dressing, which may be similar to FIG. 10, in place on a tissue site.

FIG. 11 is a schematic cross-section of an example dressing 104, which may be similar to FIG. 10, in place on a tissue site. In the example of FIG. 11, the dressing 104 has a plurality of segments 205 in the second configuration, allowing the dressing 104 to expand its depth to fit the depth of the wound cavity on the tissue site. In some embodiments, the first layer 310 of the segments 205 (e.g. the first surface 405) in the second configuration may be substantially adjacent to and/or in contact with the tissue site in the wound cavity.

Also disclosed are methods relating to the dressing embodiments described herein. For example, a method of manufacturing a dressing (e.g. similar to the embodiments described herein) may comprise: providing a segmented manifold having a first surface and a second surface opposite the first surface; providing a first layer and a second layer; and stacking and/or placing the segmented manifold between the first layer and the second layer, with the first layer adjacent to the first surface and the second layer adjacent to the second surface. Some embodiments may further comprise attaching the first surface to the first layer and/or the second surface to the second layer. In some embodiments, portions of the first layer between adjacent segments are not bonded to the adjacent segments, and portions of the second layer between adjacent segments are not bonded to the adjacent segments. In some embodiments, portions of the first layer between adjacent segments are not bonded to portions of the second layer between adjacent segments.

Some embodiments may further comprise forming one or more vertical expansion joints between adjacent segments. In some embodiments, forming vertical expansion joints may comprise forming the first layer and the second layer, each with matching folds configured to extend between adjacent segments. Some embodiments may further comprise perforating at least the first layer to form a plurality of fluid passages in at least the first layer. Some embodiments may further comprise sealing the perimeter of the dressing (e.g. coupling the first layer and second layer at the perimeter to form a perimeter flange). In some embodiments, the segmented manifold may comprise dividing lines between manifold segments, and the method may further comprise forming the first layer and the second layer with profiles (e.g. folds) matching the dividing lines. In some embodiments, forming the first layer and the second layer with profiles may comprise vac forming and/or thermoforming polymer film. In some embodiments, stacking the segmented manifold between the first and second layers may comprise aligning the profiles (e.g. folds) with the dividing lines. Some embodiments may further comprise perforating the second layer to form a second plurality of fluid passages in the second layer. In some embodiments, providing a segmented manifold may comprise cutting a sheet of manifolding material into segments with dividing lines therebetween. For example, the dividing lines may form a spiral, a radial, or a grid pattern.

Other example methods may include methods of using a dressing having a plurality of manifold segments with vertical expansion joints therebetween (e.g. similar to dressing embodiments described herein), and the methods may for example comprise: placing the dressing (e.g. in a first configuration) into proximity with a tissue site; and vertically displacing one or more manifold segments (e.g. to a second configurations) so that the segments are substantially in proximity and/or contact with the tissue site. In some embodiments, vertically displacing one or more segments may comprise pressing (e.g. downward) on the one or more segments, for example so that they extend into the cavity at the tissue site. In some embodiments, pressing downward may slide adjacent segments vertically at the vertical expansion joint. In some embodiments, the tissue site may comprise a cavity with depth, and vertically displacing one or more segments may significantly increase the amount of contact between the first surface of the dressing and the tissue site and/or the cavity depth which the dressing can match. Some embodiments may further comprise sealing (e.g. by adhesive) a perimeter of the dressing to the tissue site. Some embodiments may further comprise applying a cover or drape over the dressing (e.g. over substantially the entire second layer). Some embodiments may further comprise applying negative pressure through the manifold segments to the tissue site.

The systems, apparatuses, and methods described herein may provide significant advantages. For example, dressing embodiments with vertical expansion joints may allow the dressing to expand in depth to reach all parts of the wound bed, which may be particularly useful for deep cavity wounds. In some embodiments, the depth of the dressing may be tailored for the specific wound, without the need for one or more additional filler layers. Some embodiments of the dressing may be easily applied to the tissue site, for example requiring only a perimeter drape to seal the edges to the tissue site. Eliminating the need for a large drape may avoid application difficulties inherent to large drapes (e.g. the drape folding over and adhering to itself). Some dressing embodiments may manage significant wound depths, and allow negative-pressure therapy for deep wound cavities.

If something is described as "exemplary" or an "example", it should be understood that refers to a non-exclusive example. The terms "about" or "approximately" or the like, when used with a number, may mean that specific number, or alternatively, a range in proximity to the specific number as understood by persons of skill in the art field (for example, +/−10%). Use of broader terms such as "comprises", "includes", and "having" should be understood to provide support for narrower terms such as "consisting of", "consisting essentially of", and "comprised substantially of". Use of the term "optionally", "may", "might", "possibly", "could", "can", "would", "should", "preferably", "typically", "often" and the like with respect to any element, component, feature, characteristic, etc. of an embodiment means that the element, component, feature, characteristic, etc. is not required, or alternatively, the element, component, feature, characteristic, etc. is required, both alternatives being within the scope of the embodiment(s). Such element, component, feature, characteristic, etc. may be optionally included in some embodiments, or it may be excluded (e.g. forming alternative embodiments, all of which are included within the scope of disclosure). Section headings used herein are provided for consistency and convenience, and shall not limit or characterize any invention(s) set out in any claims that may issue from this disclosure. If a reference numeral is used to reference a specific example of a more general term, then that reference numeral may also be used to refer to the general term (or vice versa).

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing, the container, or both may be eliminated or separated from other components for manufacture or sale. In other example configurations, the controller may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims. Also, features, elements, and aspects described with respect to a particular embodiment may be combined with features, elements, and aspects described with respect to one or more other embodiments.

What is claimed is:

1. A dressing for treating a tissue site with negative pressure, the dressing comprising:
a manifold comprising a first surface and a second surface opposite the first surface, wherein the manifold further comprises a plurality of segments;
a first layer adjacent to the first surface and a second layer adjacent to the second surface, the first layer and the second layer each comprising a polymer film, wherein the first layer comprises one or more folds configured to extend between adjacent segments, and wherein the second layer comprises one or more folds configured to extend between adjacent segments;
a plurality of fluid passages in the polymer film adjacent to at least the first surface; and
one or more vertical expansion joints, wherein adjacent segments have one of the vertical expansion joints located therebetween and the vertical expansion joints are configured to allow vertical movement of the segments, wherein each of the vertical expansion joints comprises an open space between a portion of the first layer and a portion of the second layer across an entire gap between the adjacent segments.

2. The dressing of claim 1, wherein each segment of the manifold is coupled to the first layer at the first surface and to the second layer at the second surface.

3. The dressing of claim 1, wherein each of the vertical expansion joints comprises a portion of the first layer between adjacent segments which is not coupled to the adjacent segments and a portion of the second layer between the adjacent segments which is not coupled to the adjacent segments.

4. The dressing of claim 3, wherein, for each of the vertical expansion joints in a first, non-extended configuration, the portion of the first layer between adjacent segments extends along a sidewall of a first of the adjacent segments; the portion of the first layer between adjacent segments extends along a sidewall of a second of the adjacent segments; the portion of the second layer between adjacent segments extends along the sidewall of the first of the adjacent segments; and the portion of the second layer between adjacent segments extends along the sidewall of the second of the adjacent segments.

5. The dressing of claim 4, wherein, for each of the vertical expansion joints, the portion of the first layer between adjacent segments and the portion of the second layer between adjacent segments are not coupled to each other.

6. The dressing of claim 5, wherein each of the vertical expansion joints comprises a fluid bridge between adjacent segments, wherein the fluid bridge is defined between the first layer and the second layer, spans the gap between the adjacent segments, and is configured to allow fluid communication between the adjacent segments.

7. The dressing of claim 6, wherein the fluid bridge is configured to maintain open space between the first layer and the second layer regardless of expansion of dressing segments at the vertical expansion joint.

8. The dressing of claim 6, wherein the fluid bridge is configured to maintain an open fluid pathway between adjacent segments under therapeutic negative pressure.

9. The dressing of claim 6, wherein the fluid bridge comprises a support feature configured to prevent collapse of the fluid bridge under therapeutic negative pressure.

10. The dressing of claim 4, wherein the portion of the first layer between adjacent segments forms the one or more folds in the first layer, and the portion of the second layer between adjacent segments forms the one or more folds in the second layer.

11. The dressing of claim 1, wherein the segments are formed by one or more dividing lines through the manifold.

12. The dressing of claim 11, wherein the one or more dividing lines each extend from the first surface to the second surface and form separate segments of the manifold, wherein the separate segments are separated by the dividing lines.

13. The dressing of claim 1, wherein the first layer and the second layer are bonded at a perimeter of the dressing.

14. The dressing of claim 1, wherein the first layer and the second layer jointly encapsulate segments of the manifold and jointly form the one or more vertical expansion joints between adjacent segments.

15. The dressing of claim 1, wherein the one or more folds in the first layer correspond to the one or more folds in the second layer to align vertically.

16. The dressing of claim 1, wherein the manifold segments comprise open-cell foam.

17. A dressing comprising:

a segmented manifold; and one or more vertical expansion joints between segments of the manifold, wherein each of the vertical expansion joints comprises an open space between a first layer and a second layer across an entire gap between adjacent segments, wherein the first layer comprises one or more folds configured to extend between adjacent segments, and the second layer comprises one or more folds configured to extend between adjacent segments, and wherein the first layer and-the second layer are independently movable along the entire gap.

18. The dressing of claim 17, wherein a portion of the first layer is positioned adjacent to a first surface of the manifold and a portion of the second layer is positioned adjacent to a second surface of the manifold.

19. The dressing of claim 18, wherein the one or more folds in the first layer correspond to the one or more folds in the second layer to jointly form the one or more vertical expansion joints.

20. The dressing of claim 17, wherein the vertical expansion joints are configured so that each manifold segment may be displaced vertically.

21. The dressing of claim 18, wherein each segment of the manifold is coupled to the first layer at the first surface and/or to the second layer at the second surface.

22. The dressing of claim 18, wherein each of the vertical expansion joints comprises a portion of the first layer between adjacent segments which is not bonded to the adjacent segments, and a portion of the second layer between the adjacent segments which is not bonded to the adjacent segments.

23. The dressing of claim 18, wherein the first layer comprises a first plurality of fluid passages.

24. The dressing of claim 17, wherein the segments are formed by one or more dividing lines through the manifold.

25. A method of using a dressing having a plurality of manifold segments with vertical expansion joints therebetween, comprising:

placing the dressing into proximity with a tissue site, wherein the vertical expansion joints include a first layer and a second layer extending across an entire gap between adjacent manifold segments, wherein one or more folds in each of the first layer and the second layer extends between adjacent segments, and wherein an open space between the first layer and the second layer is defined across the entire gap;

vertically displacing one or more manifold segments by sliding at least one of the manifold segments vertically downward relative to another of the manifold segments so that the manifold segments are substantially in contact with the tissue site, wherein vertically displacing the one or more manifold segments includes moving the first layer and the second layer independently along the entire gap; and applying negative pressure through the manifold segments to the tissue site.

26. A method of manufacturing a dressing, comprising:

providing a segmented manifold having a first surface and a second surface opposite the first surface;

providing a first layer and a second layer;

stacking the segmented manifold between the first layer and the second layer, with the first layer adjacent to the first surface and the second layer adjacent to the second surface;

attaching the first surface to the first layer and/or the second surface to the second layer; and creating one or more folds in each of the first layer and the second layer extending between adjacent segments of the manifold;

wherein an open space is defined between a portion of the first layer and a portion of the second layer across an entire gap between adjacent segments, and wherein portions of the first layer between adjacent segments are not bonded to the adjacent segments, and portions of the second layer between adjacent segments are not bonded to the adjacent segments.

* * * * *